United States Patent [19]

Lee et al.

[11] Patent Number: 5,015,797

[45] Date of Patent: May 14, 1991

[54] ALKYLATION OF POLYCYCLIC AROMATIC COMPOUNDS TO ALKYLATES ENRICHED IN THE LINEAR- AND NEAR LINEAR-SUBSTITUTED ISOMERS

[75] Inventors: Guo-shuh J. Lee; Juan M. Garcés; Joseph J. Maj, all of Midland, Mich.

[73] Assignee: The Dow Chemical Company, Midland, Mich.

[21] Appl. No.: 458,036

[22] Filed: Dec. 28, 1989

Related U.S. Application Data

[60] Continuation-in-part of Ser. No. 422,187, Oct. 16, 1989, which is a division of Ser. No. 323,530, Mar. 14, 1989, which is a continuation-in-part of Ser. No. 123,741, Nov. 23, 1987, Pat. No. 4,891,448.

[51] Int. Cl.$^5$ .............................................. C07C 2/68
[52] U.S. Cl. .................................................. 585/467
[58] Field of Search ........................................ 585/467

[56] References Cited

U.S. PATENT DOCUMENTS

| | | | |
|---|---|---|---|
| 3,631,120 | 12/1971 | Eberly, Jr. et al. | 260/671 |
| 3,763,260 | 10/1973 | Pollitzer | 260/672 T |
| 3,888,938 | 6/1975 | Ogasawara et al. | 260/668 A |

FOREIGN PATENT DOCUMENTS

| | | |
|---|---|---|
| 0202752 | 11/1986 | European Pat. Off. . |
| 0285280 | 10/1988 | European Pat. Off. . |
| 56-133224 | 10/1981 | Japan . |
| 56-156222 | 12/1981 | Japan . |
| 58-159427 | 9/1983 | Japan . |
| 63-122635 | 5/1988 | Japan . |

*Primary Examiner*—Curtis R. Davis

[57] ABSTRACT

Polycyclic aromatic compounds, such as biphenyl, are alkylated with an alkylating agent, such as propylene, in the presence of an acidic mordenite zeolite catalyst under conditions sufficient to produce a mixture of substituted polycyclic aromatic compounds enriched in the linear- and near linear-alkylated isomers, such as p,p'- and p,m'-di(isopropyl)biphenyl. The novel acidic mordenite catalyst is characterized by its silica/alumina molar ratio, its porosity, and a Symmetry Index. Mixtures of the p,p'- and p,m'-disubstituted isomers of polycyclic aromatic compounds are useful as monomers in the preparation of improved thermotropic, liquid crystal polymers.

29 Claims, No Drawings

ALKYLATION OF POLYCYCLIC AROMATIC COMPOUNDS TO ALKYLATES ENRICHED IN THE LINEAR- AND NEAR LINEAR-SUBSTITUTED ISOMERS

This application in a continuation-in-part of application Ser. No. 07/422,187, filed Oct. 16, 1989 and now pending, which is a division of application Ser. No. 07/323,530, filed Mar. 14, 1989 and now pending, which is a continuation-in-part of application Ser. No. 07/123,741, filed Nov. 23, 1987 and now U.S. Pat. No. 4,891,448.

BACKGROUND OF THE INVENTION

This invention relates to mordenite zeolites and their use as catalysts in the alkylation of polynuclear aromatic compounds to alkylates enriched in the linear- and near linear-substituted isomers.

The linear-dialkylates of polynuclear aromatic hydrocarbons, such as 4,4'-dialkylated biphenyl or 2,6-dialkylated naphthalene, are valuable intermediates in the preparation of monomers from which thermotropic liquid crystal polymers are synthesized. Liquid crystal polymers are high molecular weight polymers which naturally exist in or can form liquid-crystal states. The liquid-crystal state is a highly anisotropic fluid state which possesses some properties of a solid and some properties of a conventional, isotropic liquid. For example, the typical liquid crystal flows like a fluid, while retaining much of the solid state molecular order. Thermotropic liquid crystals refer to those liquid crystals which are formed by the adjustment of temperature. Generally, for a molecule to possess a liquid-crystal state the molecule must be elongated and narrow, and the forces of attraction between these molecules must be strong enough for an ordered, parallel arrangement to be maintained after melting of the solid. Thus, bulky substituents positioned on the ends of an elongated molecule in a linear or near linear fashion will usually support the liquid crystal state: whereas, non-linear arrangements or the substituents will usually destroy the liquid-crystal state. Accordingly, p,p'-disubstituted aromatic compounds are likely to exhibit liquid crystalline properties, whereas m,m'- and o,o'-disubstituted aromatic compounds are not. Thermotropic, liquid crystal polymers find utility in the formation of ultra high-strength fibers and films. An overview of liquid crystals may be found in Kirk-Othmer *Encyclopedia of Chemical Technology,* 3rd ed., Volume 14, John Wiley & Sons, New York, N.Y., pp. 395–427.

Although liquid crystal polymers have excellent physical properties and are generally regarded as high performance materials, the preparation and processing of these polymers can be difficult. Linear-disubstituted polycyclic aromatic compounds, which are the building blocks for these polymers, can have low solubility in the solvents employed for polymerization. Moreover, the polymer can have a glassy transition temperature, Tg, which is greater than about 360° C, thereby necessitating the use of unconventional equipment, such as ceramic jacketed heaters, in the processing of these polymers. It would be desirable to prepare building blocks which have improved solubility. It would be more desirable if the improved building blocks yield polymers with both a substantial degree of liquid crystallinity and a somewhat lower glassy transition temperature for ease of processing.

The synthesis of linear-disubstituted polycyclic aromatic compounds is known to require many steps. For example, one group of linear monomers from which thermotropic liquid-crystal polymers are synthesized is the p,p'-dihydroxy polynuclear aromatics. Phenol, for example, is dialkylated at the ortho positions with isobutylene, and the resulting dialkylated phenol is coupled at the para position to form 3,3'5,5'-tetra(t-butyl)-4,4'-dihydroxybiphenyl. (See U.S. Pat. No. 4,108,908.) This substituted biphenyl is dealkylated to yield p,p'-dihydroxybiphenyl, which reacts with aromatic diacids and hydroxy acids to form liquid crystal polymers Aromatic diacids are also prepared in a multi-step process. p-Chlorotoluene, for example, is coupled to form 4,4'-dimethylbiphenyl, which is subsequently oxidized to 4,4'-biphenyldicarboxylic acid. (See U.S. Pat. No. 4,263,466.)

Likewise, the synthesis of near linear polycyclic aromatic diacids is known to be difficult. The near linear polycyclic aromatic compounds are described in detail hereinbelow: but briefly, they are exemplified by 4,3'-disubstituted biphenyl or 2,7-disubstituted naphthalene. For example, the near-linear polycyclic aromatic compound 4,3'-biphenyldicarboxylic acid may be prepared in four steps: 3-ethoxycyclohex-2-ene-1-one is reacted with tolyl magnesium bromide to yield 3-tolylcyclohex-2-ene-1-one, which is reacted with methyl magnesium bromide to yield 1-tolyl-3-methyl-1,3-cyclohexadiene. The latter is dehydrogenated over a carbon supported palladium catalyst to 4,3'-dimethylbiphenyl, which can be oxidized with potassium permanganate to 4,3'-biphenyldicarboxylic acid. (See G. F. Woods et al., *Journal of the American Chemical Society.* 72, (1950) 3221.)

As illustrated in the examples hereinbefore, the syntheses of dihydroxy polynuclear aromatics and diacids require considerable effort. An alternate route based on the direct alkylation of polynuclear aromatics would require fewer starting materials and fewer steps. For example, if biphenyl could be dialkylated with propylene selectively to p,p'-(diisopropyl)biphenyl, the latter could be converted directly to p,p'-dihydroxybiphenyl or to p,p'-biphenyldicarboxylic acid. Thus, the selective alkylation of polynuclear aromatic compounds would greatly simplify the syntheses of dihydroxy polynuclear aromatics, diacids and hydroxy acids which are the building locks for liquid crystal polymers.

It is known that aromatic hydrocarbons can be alkylated in the presence of acid-treated zeolite. U.S. Pat. No. 3,140,253 (1964) and U.S. Pat. No. 3,367,884 (1968) broadly teach the use of acid-treated mordenite for the alkylation of aromatic compounds. However, such alkylations are generally not selective with respect to site and number of substitutions.

More specifically, some of the prior art illustrates the use of acid-treated zeolites in the alkylation of polycyclic aromatic compounds. For example, U.S. Pat. No. 3,251,897 teaches the alkylation of naphthalene by acid-treated zeolites X, Y, and mordenite. However, the conversion of naphthalene is shown to be low, and the selectivity to di- and triisopropyl naphthalenes is low and otherwise unspecified. Japanese Patent 56-156,222 (1981) teaches the alkylation of biphenyl using silica alumina catalysts to give the monoalkylate in a para-/meta ratio of 3/2. U.S. Pat. No. 4,480,142 (1984) discloses the alkylation of biphenyl in the presence of an acid-treated montmorillonite clay to yield 2-alkylbiphenyls as the major product.

Some of the prior art describes the use of acid-treated zeolites for the preparation of dialkylates high in para isomer content. For example, Japanese Patents 56-133,224 (1981) and 58-159,427 (1983) teach the use of acid extracted mordenite for the gas phase alkylation of benzene or monoalkylbenzenes to p-dialkylbenzenes. U.S. Pat. No. 4,283,573 (1981) discloses the alkylation of phenols by use of H-mordenites to produce p-alkyl phenols with placement of the phenolic moiety at the 2-position of the alkyl chain. U.S. Pat. No. 4,361,713 (1982) describes the treatment of numerous ZSM zeolite catalysts with a halogen-containing molecule, such as HCl, or CCl4, and calcination at a temperature of from 300° C. to 600° C. to enhance the para-selective properties of such catalysts in the alkylation of benzene compounds. As illustrated with toluene, the conversion is taught to be low, while the selectivity to p-xylene is taught to be high.

Most recently, European Patent Application 0-202,752 (1986) teaches the alkylation of multi-ring aromatic hydrocarbons to alkylated derivatives high in $\beta$ and $\beta,\beta'$ isomers. The process involves contacting a multi-ring aromatic hydrocarbon with an alkylating agent other than an alcohol, such as an alkylaromatic hydrocarbon, in the presence of a medium- or large-pore, acid-treated zeolite.

Despite the numerous teachings in the prior art, there are few useful results of the alkylation of polycyclic aromatic compounds by zeolite catalysts. Such alkylations tend to give low conversion of the polynuclear aromatic compound, and a low yield of the desirable linear- and near linear-alkylates. A variety of by-products of low value is produced making the separation and isolation of products difficult, if not impractical. In the case of biphenyl, for example, such undesirable by-products include the o,p' (ortho, para'), m,m' (meta, meta') and o,o' (ortho, ortho') dialkylated isomers, as well as ortho-monoalkylated isomers, and dialkylated isomers wherein the alkyl moieties are attached to the same ring, and also trialkylated isomers. In the case of naphthalene, for example, such undesirable by-products include the 1,5-, 1,6-, 1,7-, 1,8- 2,5-, and 2,8-dialkylated isomers and dialkylates wherein the alkyl moieties are attached to the same ring, such as the 1,2-, 1,3-, and 1,4-dialkylates. Even further removed from the prior art is the ability to control the selectivity in these catalyzed alkylations to yield mixtures of predominantly the linear- and near linear-disubstituted isomers.

It would be highly desirable to find a process for the alkylation of polycyclic aromatic compounds which would give high yields of disubstituted polycyclic aromatic compounds enriched in the linear- and near linear-alkylated isomers. It would also be highly desirable if such a process yielded monomers having improved solubility for use in the preparation of thermotropic liquid crystal polymers with improved processability.

SUMMARY OF THE INVENTION

In one aspect this invention is a process of alkylating a polycyclic aromatic compound to a mixture of substituted polycyclic aromatic compounds enriched in the linear- and near linear-alkylated isomers. The process comprises contacting a polycyclic aromatic compound with an alkylating agent in the presence of a catalyst at a temperature in the range from about 200° C. to about 350° C., and an alkylating agent pressure in the range from about 10 psig to about 150 psig such that a mixture of alkylated polycyclic aromatic compounds enriched in the linear- and near linear-alkylated isomers is formed. By "enriched" it is meant that the combined selectivity to the linear- and near linear-alkylated isomers is greater than that of the prior art, or more specifically, that the ratio of the combined moles of p,p' and p,m') isomers to total dialkylates, $[p,p'+p,m']\Sigma Di$, is at least about 60 mole percent. The catalyst is an acidic mordenite zeolite having a silica/alumina molar ratio in the range from about 15:1 to about 300:1 and having a crystalline structure which is determined by X-ray diffraction to have a Symmetry Index (SI), defined hereinafter, in the range from about 1.0 to about 2.0. Surprisingly, under the conditions of this process the conversion of the polycyclic aromatic compound is higher than the conversions known heretofore. Moreover, under the conditions of this process the combined selectivity to the corresponding linear- and near linear-alkylated isomers is higher than known heretofore. Consequently, the combined yield of linear- and near linear-alkylated polycyclic aromatic products is significantly higher than the yield of such products obtained by the alkylations disclosed in the prior art.

Mixtures of linear- and near linear-alkylated polynuclear aromatic compounds prepared by the process of this invention are useful intermediates in the preparation of mixtures of monomers for thermotropic liquid crystal polymers. Moreover, the monomeric mixtures derived from the process of this invention have improved solubility over the individual pure monomers. Furthermore, the monomeric mixtures derived from the process of this invention are useful in preparing thermotropic, liquid crystal polymers with improved processability and ease of handling.

In another aspect, this invention is a novel catalyst composition comprising an acidic mordenite zeolite having a silica/alumina molar ratio in a range from about 15:1 to about 300:1, a Symmetry Index (SI) as defined hereinafter of between about 1.0 and 2.0, and a porosity such that the total pore volume is in the range from about 0.18 co/g to about 0.45 cc/g, and the ratio of the combined meso- and macropore volume to the total pore volume is in the range from about 0.25 to about 0.75. For the purposes of this invention, a micropore has a radius in the range of about 3 angstrom units (Å) to 10 Å, a mesopore has a radius in the range of 10 Å to 100 Å, and a macropore has a radius in the range of 100 Å to 1000 Å.

In a third aspect, this invention is a process of preparing the aforementioned catalyst which process comprises contacting a mordenite zeolite having a silica/alumina molar ratio of less than about 15:1 and a Symmetry Index, as determined by X-ray crystallography of less than about 1.0 with an ammonium salt and heating the ammonium-treated mordenite under conditions such that an acidic mordenite having a silica/alumina molar ratio of between about 15:1 and about 300:1 and a Symmetry Index in the range from about 1.0 to about 2.0 is formed.

The novel catalyst composition, identified hereinabove and prepared by the aforementioned process, can be usefully employed in the alkylation process of this invention.

In a fourth aspect, this invention is an isomeric mixture consisting essentially of 4,4'-dialkylated biphenyl and 4,3'-dialkylated biphenyl, obtained from an alkylation reaction. The composition of this invention is useful in preparing mixtures of monomers, such as 4,4'- and 4,3'-dihydroxybiphenyl and 4,4'- and 4,3'-biphenyl dicarboxylic acid. These monomeric mixtures have improved solubility and are useful in the synthesis of liquid crystal polymers with improved processability.

DETAILED DESCRIPTION OF THE INVENTION

The polycyclic aromatic compound of the invention is any aromatic compound containing a plurality of aromatic rings. The aromatic rings may be fused, like naphthalene, or non-fused ring assemblies, like biphenyl. The nomenclature and numbering of the fused and non-fused polycyclic compounds of this invention follow standard practice as found in *Nomenclature of Organic Chemistry*, International Union of Pure and Applied Chemistry, Butterworths, London, 1969, pp 20-31 and contains up to three rings. If non-fused, the polycyclic aromatic compound is represented by the preferred formulas:

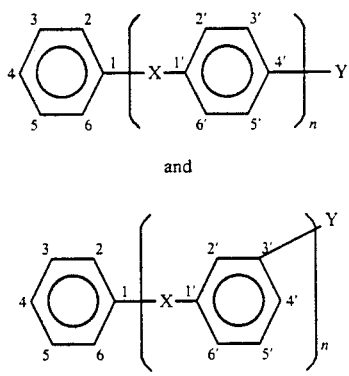

wherein n is a positive number from 1 to 3: Y is hydrogen, hydroxyl, sulfhydryl, alkyl preferably of $C_{1-10}$ carbon atoms, aliphatic alkoxy or thioalkoxy of $C_{1-10}$ carbon atoms, fluoro, chloro or bromo; and X may be absent or present. If absent, the phenyl rings are bonded at the 1,1' positions to each other. If present, X may be O, S, SO, $SO_2$, $CH_2$, $CH_2CH_2$, $CH_2CH_2CH_2$ or $CHCH_3$. In addition to being fused or non-fused, the aromatic rings may also be substituted or unsubstituted. If substituted, the substituents may be at any position provided that one of the para and one of the meta (non-fused) positions on the same ring, or one of the beta (fused) positions, are unsubstituted. If the polycyclic aromatic compound is biphenyl, for example, the ortho (2, 2', 6, 6') positions and three of the meta (3, 3', 5, 5') positions and one of the para (4, 4') positions may be substituted, provided that one meta and one para position on the same ring remain unsubstituted. If the polycyclic aromatic hydrocarbon is naphthalene, the alpha (1,4,5,8) and beta (2,3,6,7) positions may be substituted, providing at least one beta position remains unsubstituted. The substituent may be a $C_1$-$C_2$ alkyl moiety, such as methyl or ethyl: fluoro: chloro: hydroxyl; or a $C_1$-$C_2$ alkoxy. However, if the substituent is "Y" as shown in the preferred formulas, the substituent may include larger moieties as described hereinbefore. Preferably, the polycyclic aromatic compound is unsubstituted, or substituted with no greater than one $C_2$ moiety. More preferably, the polycyclic aromatic compound is unsubstituted. Examples of suitable polycyclic aromatic compounds which may be used in the invention are biphenyl, diphenyl ether, 4-hydroxy-1,140 -biphenyl, 4-phenoxy-1,1'-biphenyl, diphenylsulfide, terphenyl, tetraphenyl, diphenylmethane, 1,2-diphenylethane, 1,3-diphenylpropane, methylbiphenyls, ethylbiphenyls, 3- or 4-isopropylbiphenyl, naphthalene, methylnaphthalenes, ethylnaphthalenes, beta-isopropylnaphthalenes, and the like. Preferably, the polycyclic aromatic compound is a $C_{10}$-$C_{24}$ compound. More preferably, the polycyclic aromatic compound is an unsubstituted, fused or non-fused $C_{10-24}$ compound. Most preferably, the polycyclic aromatic hydrocarbon is biphenyl, diphenyl ether, or naphthalene.

The polycyclic aromatic compound may be used neat in a liquid state, or dissolved in a suitable solvent. Preferably, the polycyclic aromatic compound is used in a neat liquid state. If a solvent is employed, any inert solvent which solubilizes the polycyclic aromatic compound and does not hinder the alkylation reaction may be used. The preferred solvent is 1,3,5-triisopropylbenzene or decalin.

The alkylating agent suitable for alkylating the above-identified polycyclic aromatic compounds may be selected from a variety of materials, including monoolefins, diolefins, polyolefins, alcohols, alkyl halides, alkylsulfates, alkylphosphates, dialkylethers, and alkylaromatics. Exemplary of the monoolefins which may be employed in the process are ethylene, propylene, n-butene, isobutylene, 1-pentene, 1-hexene, cyclohexene, and 1-octene. 1,3-Butadiene is an example of a suitable diolefin. Alcohols, such as methanol, ethanol, isopropyl alcohol, isobutyl alcohol, pentyl alcohol, hexanol, and isohexanol, and alkyl halides, such as methyl chloride, isopropyl chloride, ethyl bromide, and methyl iodide are also suitable for use in the process. Alkylaromatics, such as xylenes, trimethylbenzenes, and the like, make suitable alkylating agents, as do ethers, such as dimethylether, diethylether, ethylpropylether, and diisopropylether. The preferred alkylating agent is a monoolefin, a diolefin or an alcohol. The more preferred alkylating agent is a monoolefin selected from the group consisting of propylene, n-butene, 1-hexene, cyclohexene, and 1-octene. Most preferably, the alkylating agent is propylene or n-butene.

The conditions which lead to alkylated products enriched in the linear isomers have already been disclosed in our copending application, U.S. Ser. No. 123,741, filed Nov. 23, 1987, incorporated herein by reference. Further enrichment of the alkylated products in the near linear isomers can be effected by selecting an acid mordenite having a $SiO_2/Al_2O_3$ molar ratio and a Symmetry Index within specified ranges, and by controlling the process conditions. Certain modifications of the catalyst preparation, described in the above-identified copending application, are useful in obtaining a catalyst having the required $SiO_2/Al_2O_3$ molar ratio and Symmetry Index. The preferred modifications of the catalyst preparation, described in detail hereinafter, include: (1) ammonium ion-exchange of the zeolite catalyst, (2) activation of the acid or ammonium ion-exchanged zeolite at a lower temperature, (3) activation of the acid or ammonium ion-exchanged zeolite under a vacuum, and (4) binding of the catalyst particles into aggregates. These preferred modifications may be employed individually or in combination. The preferred process conditions which tend to favor near linear alkylated isomers include: (1) use of a gaseous or liquid diluent, (2) use of a reaction temperature of at least about 250° C., (3) use of a low pressure of alkylating agent, and (4) use of low agitation of the reaction mixture, and preferably no agitation. A more detailed description of these variables is presented in the corresponding sections hereinbelow.

The alkylating agent may be used in an undiluted gaseous state or in a neat liquid state. As noted previously, the use of a diluent gas or solvent increases the selectivity to near linear isomers. Preferably, therefore, the alkylating agent is diluted with a diluent gas or solvent. The diluent gas may be any inert gas which is capable of penetrating the pores of the catalyst. When the inert gas penetrates the catalyst pores, the weight ratio of linear to near linear isomers is typically decreased. Suitable diluent gases include gases such as argon, nitrogen, and propane. If a solvent is employed, any inert solvent which dissolves the alkylating agent is suitable, for example, triisopropylbenzene.

The catalyst of the invention is an acid-modified zeolite with interconnecting twelve-ring and eight-ring channels. Zeolites have framework structures that are formally constructed from silicate and aluminate tetrahedra that share vertices. The tetrahedra may be linked to form pores or channels. The size of the pores is determined by the number of tetrahedra in the ring. Twelve-ring zeolites contain rings formed from twelve tetrahedra. Eight-ring zeolites contain rings formed from eight tetrahedra. The zeolites of this invention contain interconnecting twelve-ring and eight-ring channels. Examples of the zeolites suitable for use in this invention are mordenite, offretite and gmelinite. Mordenite-like zeolites, such as ECR-1 which is described in U.S. Pat. No. 4,657,748, and intergrowths of mordenite with other zeolites are also suitable catalysts; as are zeolites having a one-dimensional pore system with twelve-ring channels, such as type L or related zeolites. Preferably the catalyst is an acidic mordenite zeolite.

Mordenite is an aluminosilicate whose typical unit cell contents are assigned the formula $Na_8[(AlO_2)_8(SiO_2)_{40}]24\ H_2O$. Mordenite is the most siliceous natural zeolite with a silicon/aluminum mole ratio (Si/Al) of about 5/1. The dimensions of the twelve-ring pores are about $6.7 \times 7.0$ Å; the dimensions of the eight-ring pores are about $2.9 \times 5.7$ Å. The structure and properties of mordenite zeolite are described in *Zeolite Molecular Sieves*, by Donald W. Breck (John Wiley & Sons, 1974), at pages 122–124 and 162–163, which is incorporated herein by reference.

The catalyst of this invention is prepared from a mordenite zeolite typically containing cations of the alkali or alkaline earth metals, or alternatively ammonium ions. Preferably, the catalyst of the invention is prepared from a sodium mordenite zeolite; even more preferably, from a sodium mordenite zeolite having a Symmetry Index less than about 1.0. The Symmetry Index is a dimensionless number obtained from the X-ray diffraction pattern of the sodium mordenite being measured in the hydrated form. Standard techniques are employed to obtain the X-ray data. The radiation is the $K\alpha_1$ line of copper, and a Philips Electronics spectrometer is used. The mordenite zeolites exhibit an X-ray diffraction pattern whose diffraction peaks have d-spacings corresponding to those of crystalline mordenites as reported by J. D. Sherman and J. M. Bennett in "Framework Structures Related to the Zeolite Mordenite," *Molecular Sieves*, J. W. Meier and J. B. Uytterhoeven, eds., Advances in Chemistry Series, 121, 1973, pp. 52–65, and reproduced hereinbelow in Table I.

TABLE I

| Reflections | | | Calculated Cmmm | | X-Ray Powder Patterns - Integrated Intensities | | | | | |
|---|---|---|---|---|---|---|---|---|---|---|
| | | | | | Cmcm | | Immm | | Imcm | |
| hkl | 2θ | d | With Na+ | Without Na+ | With Na+ | Without Na+ | With Na+ | Without Na+ | With Na+ | Without Na+ |
| 110 | 6.50 | 13.578 | 163.6 | 86.1 | 163.6 | 86.1 | 163.6 | 86.1 | 163.6 | 86.1 |
| 020 | 8.62 | 10.245 | 19.6 | 26.4 | 19.6 | 26.6 | 19.6 | 26.4 | 19.6 | 26.5 |
| 200 | 9.75 | 9.065 | 100.0 | 100.0 | 100.0 | 100.0 | 100.0 | 100.0 | 100.0 | 100.0 |
| 001 | 11.76 | 7.520 | 23.6 | 19.0* | — | — | — | — | — | — |
| 011 | 12.53 | 7.060 | — | — | — | — | 4.0 | 3.2 | 33.5 | 27.0* |
| 101 | 12.73 | 6.946 | — | — | — | — | 65.8 | 53.0* | — | — |
| 220 | 13.03 | 6.789 | 0.8 | 3.5 | 0.8 | 3.5 | 0.8 | 3.5 | 0.8 | 3.5 |
| 111 | 13.45 | 6.578 | 10.7 | 8.6* | 81.7 | 65.8* | — | — | — | — |
| 130 | 13.84 | 6.392 | 21.5 | 10.0 | 21.5 | 10.0 | 21.5 | 10.0 | 21.5 | 10.0 |
| 021 | 14.60 | 6.062 | 11.3 | 9.1 | 7.7 | 6.2 | — | — | — | — |
| 310 | 15.27 | 5.796 | 6.2 | 9.8 | 6.2 | 9.8 | 6.2 | 9.8 | 6.2 | 9.7 |
| 210 | 15.30 | 5.788 | 59.6 | 48.0 | — | — | — | — | — | — |
| 121 | 15.40 | 5.749 | — | — | — | — | 17.5 | 14.1 | 12.5 | 10.1 |
| 211 | 15.90 | 5.570 | — | — | — | — | 9.2 | 7.4* | 64.7 | 52.2* |
| 040 | 17.30 | 5.122 | 0.9 | 2.0 | 0.9 | 2.0 | 0.9 | 2.0 | 0.9 | 2.0 |
| 031 | 17.53 | 5.046 | — | — | — | — | 4.3 | 3.5 | 1.1 | 0.9 |
| 221 | 17.58 | 5.039 | 6.7 | 5.4 | 5.0 | 4.0 | — | — | — | — |
| 131 | 18.20 | 4.870 | 1.6 | 1.3* | 0.4 | 0.3* | — | — | — | — |
| 301 | 18.82 | 4.711 | — | — | — | — | 7.3 | 5.9* | — | — |
| 311 | 19.32 | 4.591 | 0.9 | 0.8 | 7.0 | 5.7 | — | — | — | — |
| 400 | 19.57 | 4.532 | 0.0 | 0.3 | 0.0 | 0.3 | 0.0 | 0.3 | 0.0 | 0.3 |
| 330 | 19.60 | 4.526 | 26.2 | 27.7 | 26.2 | 27.7 | 26.2 | 27.7 | 26.2 | 27.7 |
| 240 | 19.89 | 4.460 | 2.5 | 0.6 | 2.5 | 0.6 | 2.5 | 0.6 | 2.5 | 0.6 |
| 231 | 20.09 | 4.416 | — | — | — | — | 1.6 | 1.3 | 0.3 | 0.3 |
| 321 | 20.74 | 4.280 | — | — | — | — | 0.2 | 0.2 | 0.1 | 0.1 |
| 041 | 20.97 | 4.234 | 0.0 | 0.0 | 0.2 | 0.2 | — | — | — | — |
| 420 | 21.42 | 4.145 | 5.1 | 2.1 | 5.1 | 2.1 | 5.1 | 2.1 | 5.1 | 2.1 |
| 141 | 21.54 | 4.123 | — | — | — | — | 0.2 | 0.1 | 1.7 | 1.4 |
| 150 | 22.22 | 3.997 | 31.4 | 31.3 | 31.3 | 31.3 | 31.4 | 31.3 | 31.4 | 31.2 |
| 401 | 22.89 | 3.882 | 9.6 | 7.7* | — | — | — | — | — | — |
| 331 | 22.91 | 3.878 | 2.0 | 1.6* | 0.3 | 0.2 | — | — | — | — |
| 241 | 23.17 | 3.836 | 0.2 | 0.1 | 14.5 | 11.7* | — | — | — | — |
| 411 | 23.30 | 3.814 | — | — | — | — | 1.8 | 1.4 | 11.1 | 8.9 |
| 002 | 23.64 | 3.760 | 7.2 | 4.1 | 7.2 | 4.1 | 7.2 | 4.1 | 7.2 | 4.1 |
| 421 | 24.50 | 3.630 | 1.4 | 1.2 | 1.4 | 1.1 | — | — | — | — |
| 112 | 24.55 | 3.624 | 0.0 | 0.5 | 0.0 | 0.5 | 0.0 | 0.5 | 0.0 | 0.5 |

TABLE I-continued

| Reflections | | | Calculated Cmmm | | X-Ray Powder Patterns - Integrated Intensities | | | | | |
|---|---|---|---|---|---|---|---|---|---|---|
| | | | | | Cmcm | | Immm | | Imcm | |
| hkl | 2θ | d | With Na+ | Without Na+ | With Na+ | Without Na+ | With Na+ | Without Na+ | With Na+ | Without Na+ |
| 051 | 24.72 | 3.598 | — | — | — | — | 1.0 | 0.8 | 0.0 | 0.0 |
| 510 | 24.92 | 3.570 | 0.8 | 0.1 | 0.8 | 0.1 | 0.8 | 0.1 | 0.8 | 0.1 |
| 022 | 25.21 | 3.530 | 6.0 | 2.9 | 6.0 | 2.9 | 6.0 | 2.9 | 6.0 | 2.9 |
| 151 | 25.21 | 3.530 | 6.7 | 5.4 | 0.1 | 0.1 | — | — | — | — |
| 202 | 25.63 | 3.473 | 40.7 | 38.5 | 40.7 | 38.5 | 40.7 | 38.5 | 40.7 | 38.5 |
| 341 | 25.67 | 3.467 | — | — | — | — | 0.0 | 0.0 | 5.7 | 4.6 |
| 060 | 26.07 | 3.415 | 2.0 | 2.6 | 2.0 | 2.6 | 2.0 | 2.6 | 2.0 | 2.5 |
| 440 | 26.23 | 3.394 | 0.1 | 0.0 | 0.1 | 0.0 | 0.1 | 0.0 | 0.1 | 0.0 |
| 350 | 26.25 | 3.392 | 32.3 | 21.5 | 32.3 | 21.5 | 32.3 | 21.5 | 32.1 | 21.4 |
| 431 | 26.39 | 3.375 | — | — | — | — | 0.0 | 0.0 | 0.0 | 0.0 |
| 251 | 26.63 | 3.344 | — | — | — | — | 13.9 | 11.2* | 0.8 | 0.6 |
| 222 | 27.09 | 3.289 | 2.7 | 0.7 | 2.7 | 0.7 | 2.7 | 0.7 | 2.7 | 0.7 |
| 501 | 27.28 | 3.266 | — | — | — | — | 25.3 | 20.4* | — | — |
| 132 | 27.50 | 3.241 | 7.7 | 3.5 | 7.7 | 3.5 | 7.7 | 3.5 | 7.7 | 3.5 |
| 511 | 27.63 | 3.225 | 4.3 | 3.4 | 28.7 | 23.1 | — | — | — | — |
| 530 | 27.83 | 3.203 | 16.1 | 10.1 | 16.1 | 10.1 | 16.1 | 10.1 | 16.1 | 10.1 |
| 260 | 27.89 | 3.196 | 0.1 | 0.0 | 0.1 | 0.0 | 0.1 | 0.0 | 0.1 | 0.0 |
| 312 | 28.27 | 3.154 | 0.3 | 1.1 | 0.3 | 1.1 | 0.3 | 1.1 | 0.3 | 1.1 |
| 521 | 28.66 | 3.112 | — | — | — | — | 3.3 | 2.7 | 2.6 | 2.1 |
| 061 | 28.68 | 3.109 | 0.5 | 0.4 | 2.4 | 1.9 | — | — | — | — |
| 441 | 28.83 | 3.094 | 0.1 | 0.1 | 2.1 | 1.7 | — | — | — | — |
| 351 | 28.85 | 3.092 | 3.5 | 2.8 | 0.4 | 0.3 | — | — | — | — |
| 161 | 29.11 | 3.065 | — | — | — | — | 1.4 | 1.1 | 5.2 | 4.2 |
| 042 | 29.44 | 3.031 | 0.0 | 0.3 | 0.0 | 0.3 | 0.0 | 0.3 | 0.0 | 0.3 |
| 600 | 29.54 | 3.022 | 0.2 | 0.4 | 0.2 | 0.4 | 0.2 | 0.4 | 0.2 | 0.4 |
| 531 | 30.31 | 2.947 | 0.9 | 0.7* | 0.2 | 0.1* | — | — | — | — |
| 261 | 30.36 | 2.941 | 1.4 | 1.1* | 3.8 | 3.1* | — | — | — | — |
| 620 | 30.82 | 2.898 | 0.9 | 0.2 | 0.9 | 0.2 | 0.9 | 0.2 | 0.9 | 0.2 |
| 402 | 30.87 | 2.894 | 7.2 | 4.2 | 7.2 | 4.2 | 7.2 | 4.2 | 7.3 | 4.2 |
| 332 | 30.89 | 2.892 | 4.1 | 5.5 | 4.1 | 5.5 | 4.1 | 5.5 | 4.1 | 5.5 |
| 170 | 30.92 | 2.890 | 0.6 | 0.1 | 0.6 | 0.1 | 0.6 | 0.1 | 0.6 | 0.1 |
| 242 | 31.08 | 2.875 | 1.8 | 0.5 | 1.8 | 0.5 | 1.8 | 0.5 | 1.8 | 0.5 |
| 451 | 31.72 | 2.818 | — | — | — | — | 2.5 | 2.1* | 0.1 | 0.1 |
| 601 | 31.89 | 2.804 | 8.0 | 6.4* | — | — | — | — | — | — |
| 422 | 32.11 | 2.785 | 0.1 | 0.1 | 0.1 | 0.1 | 0.1 | 0.1 | 0.1 | 0.1 |
| 611 | 32.20 | 2.778 | — | — | — | — | 1.4 | 1.1 | 10.1 | 8.1* |
| 361 | 32.35 | 2.765 | — | — | — | — | 0.2 | 0.2 | 0.4 | 0.3* |
| 541 | 32.48 | 2.754 | — | — | — | — | 0.1 | 0.0 | 9.1 | 7.4* |
| 152 | 32.67 | 2.739 | 0.7 | 0.1 | 0.7 | 0.1 | 0.7 | 0.1 | 0.7 | 0.1 |
| 071 | 32.80 | 2.728 | — | — | — | — | 1.1 | 0.9 | 1.8 | 1.4 |
| 460 | 32.81 | 2.727 | 1.6 | 0.6 | 1.6 | 0.6 | 1.6 | 0.6 | 1.5 | 0.6 |
| 550 | 32.96 | 2.716 | 0.9 | 1.4 | 0.9 | 1.4 | 0.9 | 1.4 | 0.9 | 1.4 |
| 621 | 33.10 | 2.704 | 2.0 | 1.6* | 1.5 | 1.2* | — | — | — | — |
| 171 | 33.18 | 2.697 | 1.3 | 1.0* | 1.7 | 1.4* | — | — | — | — |
| 370 | 34.00 | 2.634 | 1.6 | 0.7 | 1.6 | 0.7 | 1.6 | 0.7 | 1.6 | 0.6 |
| 271 | 34.30 | 2.612 | — | — | — | — | 0.2 | 0.1 | 0.0 | 0.0 |
| 640 | 34.43 | 2.603 | 0.2 | 0.0 | 0.2 | 0.0 | 0.2 | 0.0 | 0.2 | 0.0 |
| 631 | 34.55 | 2.594 | — | — | — | — | 0.0 | 0.0 | 0.0 | 0.0 |
| 512 | 34.61 | 2.589 | 2.4 | 0.9 | 2.4 | 0.9 | 2.4 | 0.9 | 2.4 | 0.9 |

*Calculated reflections which may distinguish among the various framework structures.
Reproduced from J. D. Sherman and J. M. Bennett in "Framework Structures Related to the Zeolite Mordenite," Molecular Sieves, W. M. Meier and J. B. Uytterhoeven, eds., Advances in Chemistry series, American Chemical Society, 1973, p. 56–59.

The Symmetry Index is defined as the sum of the peak heights of the [111](13.45, 2θ) and [241](23.17 2θ) reflections divided by the peak height of the [350] (26.25 2θ) reflection. Preferably, the Symmetry Index of the sodium mordenite ranges from about 0.50 to about 1.0. More preferably, the Symmetry Index of the sodium mordenite ranges from about 0.60 to about 1.0.

Four ordered crystalline structures have been proposed to describe the X-ray diffraction data available for natural and synthetic mordenite zeolites. (J. D. Sherman and J. M. Bennett, op.cit., p. 53.) The symmetries of these four structures are Cmcm, Cmmm, Imcm, and Immm as these terms are defined by N. F. M. Henry and K. Lonsdale in *International Tables for X-ray Crystallography*, 3rd Ed., Volume 1, Kynoch Press (1969). X-ray diffraction data indicate that mordenites are either physical admixtures or intergrowths of the Cmmm, Imcm, or Immm structures with the Cmcm structure. Thus, mordenites can be generally described as having a crystalline structure comprising a matrix of Cmcm symmetry having dispersed therein domains of Cmmm, Imcm, or Immm symmetry, or mixtures thereof. Preferably, the mordenite of this invention has a crystalline structure comprising a matrix of Cmcm symmetry having dispersed therein domains of Cmmm symmetry. The Symmetry Index is related to the symmetries of the crystals present in the mordenite sample. A Symmetry Index in the range from about 0.60 to about 1.0 provides the optimum sodium mordenite as starting material for the process of this invention.

The crystallite size of the original sodium mordenite may be any size which yields a catalyst selective for alkylated polycyclic aromatic compounds enriched in the linear- and near linear-substituted isomers. Typically, the crystallite size may be in the range from about 500 Å to about 5000 Å. Preferably, the crystallite size is in the range from about 500 Å to about 2000 Å; more preferably, from about 800 Å to about 1500 Å. Generally, the crystallites form aggregates which may be used as such or bound into larger particles for the process of this invention. For example, extrudate can be made for a packed-bed reactor by compressing the aggregates without binder into suitable larger-sized agglomerates. Alternatively, the extrudate can be made via use of binders well-known to those in the art. It has been found that extrudates between about 1/32 inch and about ½ inch in diameter improve the combined selectivity to linear- and near linear-substituted isomers. The preferred extrudate size ranges from about 1/16 inch to about ¼ inch in diameter.

The original sodium mordenite zeolite described hereinabove, or its equivalent, is treated to obtain the catalyst of the invention for use in the alkylation process. The treatment involves contacting the mordenite with acid or an ammonium salt. Preferably, the treatment involves contacting the mordenite with an ammonium salt to convert the sodium mordenite into the ammonium form, and calcining the ammonium-treated mordenite to convert it into an acid mordenite.

The initial acid treatment serves to remove most of the sodium ions, or their equivalents, from the original mordenite. The treatment may remove a portion of the aluminum ions as well. Inorganic acids and organic acids are suitable compounds from which the hydrogen ions are obtained for the acid treatment. Examples of such acids are hydrochloric acid, hydrobromic acid, sulfuric acid, phosphoric acid, nitric acid, acetic acid, oxalic acid, and the like. Among these inorganic acids, hydrochloric acid is preferred. The most preferred initial treatment, as it favors the formation of near linear isomers in the alkylation process of this invention, involves ion exchange with ammonium salts, such as ammonium chloride and ammonium nitrate. By this method the sodium ions or their equivalents are removed, but the aluminum ions are not displaced. On heating the ammonium-exchanged mordenite, ammonia is given off and the mordenite is converted into the acid form.

Typically, in the initial acid or ammonium treatment the original sodium mordenite is slurried with an aqueous solution of the acid or ammonium salt. The solution may have any concentration, providing the catalyst obtained possesses the properties and activity of the catalyst of this invention, these being described hereinafter. Preferably, the concentration of the aqueous solution is in the range from about 0.01N to about 6N; more preferably in the range from about 0.5N to about 3.0N. The relative quantities of aqueous acid or ammonium salt solution to mordenite solid which are employed may vary. Typically, the ratio is less than about 15 cc acid of ammonium salt solution per gram mordenite solid. Preferably, the ratio is in the range from about 5 cc solution per gram mordenite solid to about 10 cc solution per gram mordenite solid. The temperature and the duration of the contact of the mordenite with the acid or salt solution may also vary. Preferably, the mordenite is contacted with the acid or salt solution at a temperature in the range from about 10° C. to about 100° C. Generally, the contact time between the solution and the mordenite may vary from about 5 minutes to about several hours. It is important that there be sufficient time for the solution to contact all of the mordenite particles. Preferably, the contact time is from about 5 minutes to about 60 minutes. The contacting with acid solution or ammonium salt solution, as described herein, may be repeated if desired. Afterwards, the mordenite is washed in water one or more times in order to rinse away soluble species from the mordenite. Preferably, the water wash is carried out at ambient temperature. Optionally, subsequent to the water wash the mordenite is dried in air at a temperature in the range from about 20° C. to about 150° C.

In the preferred treatment, following the exchange with acid or ammonium salt and drying in air, the mordenite zeolite is calcined in air or heated in a vacuum or an inert atmosphere, such as nitrogen. Preferably, the mordenite zeolite is calcined in a vacuum, as this tends to increase the combined selectivity to linear and near linear isomers in the alkylation process of this invention. This heating procedure has a two-fold purpose. First, the heating drives off ammonia, thereby converting an ammonium-exchanged mordenite into an acidic mordenite. Secondly, it is believed that this heat treatment dislocates a portion of the aluminum from the zeolite framework; however, such a theory should not be taken as limiting of the scope of the invention. Typically, the temperature of the calcination or heating may range from about 250° C. to about 700° C. Preferably, the temperature of the calcination or heating is in the range from about 300° C. to about 600° C. More preferably, the temperature is in the range from about 350° C. to about 550° C.

After calcining the acid or ammonium-treated mordenite described hereinabove, the mordenite may be subjected to an additional acid treatment for the purpose of further dealumination; however, this treatment is not required and is not preferred. The second acid treatment comprises contacting the calcined mordenite with a strong acid. For the purposes of this invention a "strong" acid is defined as an acid which reacts essentially completely with the solvent to give the conjugate acid of the solvent. For example, if gaseous hydrogen chloride is dissolved in water, the acid-base reaction is complete to give the conjugate acid $H_3O+$ and $Cl-$. Preferably, the strong acid is an inorganic acid. More preferably, the strong acid is nitric acid, hydrochloric acid, or sulfuric acid. Most preferably, the strong acid is nitric acid. The concentration of the strong acid will vary depending on the acid selected. In general, the acid is employed in an aqueous solution of any concentration which provides for the extraction of aluminum from the calcined acidic mordenite, as described hereinafter. With nitric acid, for example, the concentration of the acid in the aqueous solution is preferably in the range from about 2N to about 15N. More preferably, the concentration of the acid is in the range from about 4N to about 12N. Most preferably, the concentration of the acid is in the range from about 6N to about 8N. The aqueous acid solution and the calcined mordenite are contacted in any ratio that provides the catalyst of the invention. Preferably, the ratio of aqueous acid solution to mordenite is in the range from about 3 cc acid solution per gram mordenite to about 10 cc acid solution per gram mordenite. More preferably, the ratio is about 5 cc acid solution per gram mordenite. The temperature and the duration of the contact may vary depending on the acid selected. Preferably, the mordenite is contacted with the acid solution at a temperature in the range from about ambient temperature taken as 22° C. to about 220° C. More preferably, the mordenite and the acid are contacted at a temperature which allows for boiling of the aqueous acid under atmospheric conditions. Preferably, the duration of the contact is from about 1 hour to about 6 hours; more preferably, from about 1 hour to about 3 hours; most preferably, for about 2 hours. When the contacting with strong acid is complete, the mordenite is filtered and washed repeatedly with water until the washings are acid-free. Preferably, the washed mordenite is heat treated and contacted with strong acid more than once. Lastly, the washed acidic mordenite zeolite is dried for several hours at a temperature in the range from about 100° C. to about 150° C. to remove physically adsorbed water. The dried acidic mordenite is activated by heating for about 2 hours at a temperature in the range from about 250° C. to about 700° C. This activation may drive off more strongly bound water and any residual adsorbates.

After the original sodium mordenite is treated with acid or ammonium salts, calcined, and optionally retreated with strong acid, according to the process of this invention, an acidic mordenite catalyst is obtained which is capable of converting a polycyclic aromatic compound in a high conversion to a mixture of substituted polycyclic aromatic compounds enriched in the linear- and near linear-alkylated isomers. This catalyst exhibits special characteristics by which it may be identified, specifically, the silica/alumina molar ratio, and the Symmetry Index and porosity as defined hereinafter.

As a result of the acid extractions or ammonium treatment and heating, the silica/alumina molar ratio ($SiO_2/Al_2O_3$) of the acidic mordenite catalyst is increased over that of the original sodium mordenite. Specifically, the acidic mordenite catalyst has a silica/alumina molar ratio of at least 15:1. Preferably, the silica/alumina molar ratio is in the range from about 15:1 to about 300:1, more preferably, in the range from about 15:1 to about 150:1; most preferably in the range from about 15:1 to about 50:1. The lower $SiO_2/Al_2O_3$ molar ratios imply a higher aluminum content in the dealuminated mordenite catalyst. A higher aluminum content is correlated with an increase in the combined selectivities to the linear and near linear isomers in the alkylation process of this invention.

As a further result of the acid extractions and calcination, the Symmetry Index of the mordenite catalyst is increased over that of the original mordenite. The Symmetry Index is as defined hereinbefore. Since the Symmetry Index is derived from X-ray data, the Index is related to the proportion of Cmcm and Cmmm, Imcm, or Immm symmetries present in the catalyst. The increase in the Symmetry Index is indicative of the enrichment of the catalyst in the Cmcm component. A Symmetry Index of at least about 1.0 results in catalysts capable of achieving high yields of the linear- and near linear-alkylated polycyclic aromatic compounds. The preferred Symmetry Index ranges from about 1.0 to about 2.0. More preferred is a Symmetry Index in the range from about 1.5 to about 2.0.

A third property of the acidic mordenite catalyst, by which it is identified, is the porosity. All zeolites possess pores which form as a natural consequence of zeolite crystal growth. New pores or modifications of existing pores can occur on treating the zeolites, for example, with heat or acid as in the process of this invention. Typically, pores are classified into micropores, mesopores and macropores. For the purposes of this invention a micropore is defined as having a radius in the range from about 3 Angstrom units (3 Å) to 10 Å. Likewise, a mesopore is defined as having a radius in the range from 10 Å to 100 Å, while a macropore is defined as having a radius from 100 Å to 1000 Å. After treatment with ammonium salts, calcination, and optionally strong acid treatment, the acidic mordenite catalyst of this invention possesses micro-, meso- and macropores. The porosity of the catalyst may be distinguished by the total pore volume defined as the sum of the volumes of the micro-, meso-, and macropores per gram catalyst. A catalyst of this invention has a total pore volume sufficient to provide a high combined yield of linear- and near linear-alkylated isomers in the alkylation of a polycyclic aromatic compound. Preferably, the total pore volume is in the range from about 0.18 cc/g to about 0.45 cc/g. The porosity may be further distinguished by the relative distribution of meso- and macropores, as found in the ratio of the combined meso- and macropore volume to the total pore volume. A catalyst of this invention has a ratio of combined meso- and macropore volume to total pore volume sufficient to provide a high combined yield of linear and near linear-alkylated isomers in the alkylation of a polycyclic aromatic compound Preferably, the ratio of the combined meso- and macropore volume to total pore volume is in the range from about 0.25 to about 0.75.

The measurement of the porosity, described hereinabove, is derived from surface area and pore volume measurements of mordenite powders obtained on any suitable instrument, such as a Quantachrome Digisorb-6 unit, using nitrogen as the adsorbate at the boiling point of nitrogen, 77 K. The total pore volume (VT) is derived from the amount of nitrogen adsorbed at a relative pressure close to unity. It is accepted that this volume constitutes pores of less than 1000 Å in radius. As stated earlier, for the purposes of this invention pores with radius of 10 Å or less are called micropores. Pores with radius from 10 Å to 100 Å are called mesopores, and pores with radius from 100 Å to 1000 Å are called macropores. Pores with radius in the 10 Å to 1000 Å range are known in the literature as "transitional pores." The micropore volume (Vm) in the presence of "transitional pores" is obtained by the t-method. The difference between the total pore volume and the micropore volume is the transitional pore volume, ($V_t = V_T - V_m$). The cumulative pore distribution in the transitional pore range is used to calculate the relative volume contributions of mesopores and macropores. For example, the mesopore volume is calculated by multiplying the transitional pore volume by the fraction of the cumulative pore volume from 10 Å to 100 Å, ($V_{me} = V_t f_{me}$). The macropore volume is then simply obtained by subtracting the mesopore volume from the transitional volume, ($V_{ma} = V_t - V_{me}$). This approach ensures that the equation $V_T = V_m + V_{me} + V_{ma}$ is satisfied. The adsorption isotherms obtained for the mordenite catalysts of this invention are of Type I, which are described by the Langmuir equation. The Langmuir surface area is obtained from such equation. The methods used to obtain surface areas and pore volumes are described by S. Lowell in *Introduction to Powder Surface Area* (John Wiley and Sons, 1979), or in the manuals provided with the Digisorb-6 instrument made by the Quantachrome Corporation.

The acidic mordenite catalyst, identified hereinabove, is capable of adsorbing biphenyl into the intracrystalline pore system, and conversely desorbing biphenyl. Biphenyl adsorption is effected by exposing the acidic mordenite to biphenyl vapors at 100° C. for a time sufficient to obtain near constant weight. Preferably, the adsorption capacity of the acidic mordenite for biphenyl is about 5 weight percent. More preferably, the capacity is about 10 weight percent. Biphenyl desorption is effected by heating the mordenite-biphenyl sample in a dynamic helium atmosphere from 25° C. to about 1000° C. at a heating rate of about 10° C./minute. The desorption of biphenyl may be followed experimentally by thermal gravimetric analysis combined with gas phase chromatography and mass spectrometry (TGA-GC-MS). It is found that weakly adsorbed biphenyl produces a weight loss at temperatures below about 300° C: whereas, strongly adsorbed biphenyl produces a weight loss at temperatures from about 300° C. to as high as 1000° C. The amount of strongly adsorbed biphenyl is estimated by subtracting the amount of weakly adsorbed biphenyl from the total amount of biphenyl desorbed from the sample. A fully treated mordenite catalyst of this invention exhibits a sharp weight loss at temperatures below about 300° C., and little or no weight loss from 300° C. to 1000° C. In contrast, acid-exchanged mordenite exhibits a sharp weight loss at temperatures below about 300° C., and a second weight loss starting at about 300° C and extending to 1000° C. It is believed that the weakly adsorbed biphenyl is located in sites from which there is relatively easy exit; whereas the strongly adsorbed biphenyl is located in sites from which there is relatively difficult exit. Thus, the acidic mordenite catalyst of this invention provides easy access and egress to adsorbed biphenyl. Such a theory, however, should not be construed to be binding or limiting of the scope of the invention.

The ratio of the polycyclic aromatic compound to catalyst may be any weight ratio which produces alkylates enriched in the linear- and near linear-substituted isomers. Preferably, the weight ratio of aromatic compound to catalyst is in the range from about 0.1:1 to about 2000:1. More preferably, the weight ratio is in the range from about 10:1 to about 500:1. Most preferably, the ratio is in the range from about 50:1 to about 100:1. Below the preferred lower limit of 0.1:1, the yield of linear- and near linear-substituted products may be reduced. Above the preferred upper limit of 2000:1, the conversion of the polycyclic aromatic compound may be low.

The ratio of polycyclic aromatic compound to alkylating agent may vary depending on the number of unsubstituted para and meta (unfused), or beta (fused), positions on the aromatic compound. For example, if the aromatic compound to be alkylated has only one unsubstituted para and one unsubstituted meta position, the ratio of alkylating agent to polycyclic aromatic compound is 1:1. If the polycyclic aromatic compound has two open para positions, the ratio is 2:1. The alkylating agent may be introduced to the reaction all at once, as in the case of a liquid alkylating reagent. Alternatively, the alkylating agent may be introduced to the reaction on demand until the desired degree of conversion is achieved, as in the case of a gaseous alkylating agent which is continuously fed into the reactor.

The contacting of the polycyclic aromatic compound with the alkylating agent in the presence of the catalyst may occur in a reactor of any configuration. Batch-type and continuous reactors, such as fixed-bed, slurry bed, fluidized bed, catalytic distillation, or countercurrent reactors, are suitable configurations for the contact. Preferably, the reactor is fit with a means for observing and controlling the temperature of the reaction, a means for observing and measuring the pressure of the reaction, and optionally a means for agitating the reactants. Preferably, the agitation is reduced or eliminated altogether, as the lack of agitation is correlated with an increase in the combined selectivity to the linear- and near linear-alkylated isomers.

The polycyclic aromatic compound may be in the molten, liquid form or in solution. The alkylating agent may be introduced into the reactor in the liquid or gaseous state, and may be added all at once at the start of the reaction, or fed continuously on demand from the reaction. The catalyst may be used in various forms, such as a fixed-bed, moving bed, fluidized bed, in suspension in the liquid reaction mixture, or in a reactive distillation column.

The contacting of the reactants in the presence of the catalyst may occur at any temperature or pressure which will produce as the major products the substituted polycyclic aromatic compounds enriched in the linear and near linear-alkylated isomers. Suitable temperatures are those which are high enough to promote some isomerization of the linear isomers to the near linear isomers. Typically, the temperature is in the range from about 100° C. to about 400° C. Preferably, the temperature is in the range from about 200° C. to about 350° C. More preferably, the temperature is in the range from about 250° C. to about 300° C. Below the preferred lower limit of 200° C. the isomerization reaction may proceed slowly. Above the typical upper limit of 400° C., the alkyl groups may crack, such as in the cracking of isopropyl moieties to ethylene moieties. Moreover, above the preferred upper limit of 350° C. the alkyl groups may scramble extensively upsetting the selectivity for the linear and near linear isomers. The typical alkene pressure in the reactor falls in the range from about 10 psig to about 500 psig. Preferably, the alkene pressure is in the range from about 10 psig to about 150 psig. More preferably, the pressure is in the range from about 10 psig to about 50 psig. Below the preferred lower limit of 10 psig the catalyst may begin to lose selectivity for linear and near linear isomers. Above the typical upper limit of 500 psig the preferred olefin alkylating agent will polymerize severely, and above the preferred upper limit of 150 psig the selectivity to the near linear isomers may be decreased.

The polycyclic aromatic compound, alkylating agent, and catalyst are contacted for a time sufficient to convert the polycyclic aromatic compound to alkylated products, and sufficient to produce the desired yield of linear- and near linear-alkylated aromatic compounds. Generally, the contact time will depend on other reaction conditions, such as temperature, pressure and reagent/catalyst ratios. In a typical stirred batch reactor, for example, the reaction time is preferably in the range from about 0.1 hour to about 40 hours. More preferably, the reaction time is in the range from about 0.5 hour to about 20 hours.

The products of this invention include a mixture of alkylated polycyclic aromatic compounds enriched in the linear- and near linear-alkylated isomers. The linear-alkylated isomers are those in which the alkyl group(s) is (are) attached at the ends of the molecule, thereby yielding the product of smallest critical diameter. In the alkylation of biphenyl, for example, one such enriched product is the p,p'-dialkylate (4,4'-dialkylate). Likewise, in the alkylation of terphenyl, one such enriched product is the p',p''-dialkylate (4',4''-dialkylate). In the alkylation of naphthalene, a fused ring system, one such enriched product is the 2,6-dialkylate. Such products provide the smallest critical diameter to the alkylated molecule. The near linear-alkylated isomers are those in which the alkyl group(s) is (are) attached so as to yield the molecule of next to smallest critical diameter. For example, in the alkylation of biphenyl the near linear isomer is the p,m'-dialkylate (4,3'-dialkylate). Likewise, in the alkylation of naphthalene, the near linear isomer is the 2,7-dialkylate. All other alkylated products, such as the p,o'-dialkylate of biphenyl or the m,m'-dialkylate of biphenyl, or the 2,5-dialkylate of naphthalene, yield molecules of larger critical diameter.

For the purposes of this invention, the term "conversion" refers to the mole percent of polycyclic aromatic compound which reacts to form alkylated products. Typically, in the batch reaction, the conversion achieved in the practice of this invention is at least about 50 mole percent. Preferably, the conversion is at least about 65 mole percent. More preferably, the conversion is at least about 80 mole percent. Most preferably, the conversion is at least about 95 mole percent.

Likewise, the term "selectivity" refers to the mole percent of reacted polycyclic aromatic compound which is converted to a specific alkylated product. For example, in the practice of this invention biphenyl is converted to alkylates enriched in the p,p'-dialkylate, 4,4'-di(1-methylethyl)-1,1'-biphenyl and in the p,m'-dialkylate, 4,3'-di(1-methylethyl)-1,1'-biphenyl. Smaller amounts of the 3- and 4-monoalkylated isomers are obtained. Even smaller amounts of the 2-monoalkylated isomer and the dialkylates in which both alkyls are attached to one ring are obtained. Typically, the selectivity to total dialkylated biphenyls ranges from about 25 mole percent to about 80 mole percent. Typically, the selectivity to p,p'-dialkylated biphenyls achieved in the practice of this invention is at least about 20 mole percent: preferably, at least about 40 mole percent: more preferably, at least about 50 mole percent. Typically, the combined selectivity to p,p'- and p,m'-dialkylated biphenyls achieved in the practice of this invention is at least about 25 mole percent: preferably, at least about 45 mole percent; more preferably, at least about 60 mole percent. Typically, the selectivity to linear alkylates achieved in the practice of this invention is at least about 20 mole percent: preferably, at least about 40 mole percent: more preferably, at least about 50 mole percent; most preferably, at least about 70 mole percent. Typically, the combined selectivity to linear and near linear alkylates achieved in the practice of this invention is at least about 25 mole percent: preferably, at least about 45 mole percent; more preferably, at least about 60 mole percent.

The selectivity for p,p'-dialkylate may also be expressed as the product $100 \times p,p'/\Sigma Di \times \Sigma Di/TA$. The first factor is the ratio $p,p'/\Sigma Di$, wherein $p,p'$ represents the moles of p,p'-dialkylated isomers and $\Sigma Di$ represents the total number of moles of dialkylated isomers. This ratio indicates the fraction of the total dialkylates which are p,p' isomers. Typically, in the process of this invention the p,o' and o,o' isomers are not formed; therefore, the total dialkylates contain only the p,p', p,m', and m,m' isomers. In contrast, in processes of the prior art all of the aforementioned isomers are typically formed. Typically, the $p,p'/\Sigma Di$ ratio, expressed as a percentage, is at least about 40 mole percent. Preferably, $p,p'/\Sigma Di$ is at least about 60 mole percent; more preferably, at least about 70 mole percent; most preferably, at least about 80 mole percent. The second factor is the ratio $\Sigma Di/TA$, wherein $\Sigma Di$ is defined as above and TA is the total number of moles of all alkylated products. This ratio indicates the fraction of all alkylated products which are dialkylates. Typically, this ratio, expressed as a percentage, is at least about 15 mole percent. Preferably, $\Sigma Di/TA$ is at least about 30 mole percent; more preferably, at least about 50 mole percent; most preferably, at least about 70 mole percent.

The combined selectivity for p,p'- and p,m'-dialkylates may also be expressed as the product $100 \times [p,p'+p,m']/\Sigma Di \times \Sigma Di/TA$. The first factor is the ratio $[p,p'+p,m']/\Sigma Di$, wherein $[p,p'+p,m']$ represents the combined moles of p,p'- and p,m'-dialkylated isomers and $\Sigma Di$ represents the total number of moles of dialkylated isomers, as defined hereinabove. This ratio indicates the fraction of the total dialkylates which are the p,p' and p,m' isomers. Typically, this ratio, expressed as a percentage, is at least about 60 mole percent. Preferably, $[p,p'+p,m']/\Sigma Di$ is at least about 70 mole percent: more preferably, at least about 90 mole percent. The second factor is the ratio $\Sigma Di/TA$, wherein $\Sigma Di$ is defined as above and TA is the total number of moles of all alkylated products. This ratio indicates the fraction of all alkylated products which are dialkylates. Typically, this ratio, expressed as a percentage, is at least about 15 mole percent. Preferably, $\Sigma Di/TA$ is at least about 30 mole percent: more preferably, at least about 50 mole percent: most preferably, at least about 70 mole percent.

Another measure indicative of the formation of linear and near linear isomers is the p,p'/p,m' weight ratio. Typically, this ratio can vary widely depending upon the specific catalyst and process conditions employed. For example, the ratio may be as low as 0.3 or as high as 17. Preferably, the p,p'/p,m' weight ratio is in the range from about 1.0 to about 6.0, more preferably, from about 1.2 to about 3.0.

The concept of simultaneous high conversion and high selectivity to the linear- and near linear-alkylated polycyclic aromatic compounds may be expressed conveniently in terms of yield. For the purposes of the present invention, the term "yield" refers to the numerical product of conversion and selectivity. For example, a process according to the present invention operating at a conversion of 0.982, or 98.2 percent, and a combined selectivity to linear- and near linear-alkylated isomers of 0.650, or 65 percent, would have a combined yield of the linear and near linear isomers of 0 638, or 63.8 percent, which is the numerical product of 0.982 and 0.650. Typically, the yield of total dialkylates achieved in the process of this invention is at least 20 mole percent: preferably, at least 60 mole percent: more preferably, at least 75 mole percent. In contrast to the alkylations of the prior art, the process of the present invention may be operated to give higher yields of the linear alkylated isomers. Typical yields of the linear isomers are at least about 10 mole percent: preferably, at least about 40 mole percent: more preferably, at least about 55 mole percent and most preferably, at least about 70 mole percent. Advantageously, the process of the present invention may be operated to give higher combined yields of the linear- and near linear-alkylated isomers. A typical combined yield of the linear- and near linear-alkylated isomers is at least about 20 mole percent. Preferably, the combined yield of linear- and near linear-alkylated isomers is at least bout 40 mole percent, more preferably, at least about 55 mole percent, most preferably, at least about 70 mole percent.

Following the alkylation of the polycyclic aromatic compound, the product mixture may be separated by standard techniques, such as distillation, melt crystallization, or solvent-assisted recrystallization. In the case of a product mixture containing biphenyl and its propylated derivatives, distillation is a convenient method of separating the products. Biphenyl may be removed in a first distillation column: 3-(1-methylethyl)-1,1'-biphenyl, 4-(1-methylethyl)-1,1'-biphenyl, and 3,3'-di(1-methylethyl)-1,1'-biphenyl may be removed in a second distillation column. The bottoms may be transported to a third distillation column from which enriched 4,4'- and 4,3'-di(1-methylethyl)-1,1'-biphenyls are distilled off. The final residuals contain small amounts of triisopropylbiphenyls. If desired, the p,p'-dialkylate may be obtained in a purity greater than 99 weight percent by melt recrystallization of the p,p'- and p,m'-fraction. The residue is enriched in p,m'-dialkylate.

Mixtures of 4,4'- and 4,3'-dialkylated biphenyls may be used to prepared the corresponding mixtures of dihydroxybiphenyls or mixtures of biphenyl dicarboxylic acids. These latter mixtures are excellent monomers for thermotropic liquid crystal polymers. Advantageously, the monomeric mixtures have improved solubility over the individual pure isomers in the solvents of polymerization. More advantageously, the polymers obtained from these 4,4'- and 4,3'- mixtures have a glassy transition temperature which is above about 220° C. but below about 360° C.; thus, the polymers do not require unconventional processing equipment and are easy to handle. The degree of liquid crystallinity of these polymers will depend upon the weight percentage of the 4,3'- isomer. Typically, the higher the weight percentage of the 4,3'- isomer, the lower the degree of liquid crystallinity. At lower percentages the polymers exhibit a significant degree of liquid crystallinity and may be used in high performance materials.

2-, 3-, and 4-Monoalkylates and residual dialkylates obtained from the process of this invention may be used as chemical intermediates, as high temperature heat-transfer fluids, or as solvents. Alternatively, these by-products and any triisopropylbiphenyls may be converted via transalkylation with benzene to valuable biphenyl and cumene.

Specific Embodiments

The following examples are given to illustrate the catalyst and the process of this invention and should not be construed as limiting its scope. All percentages in the examples are mole percent unless otherwise indicated.

EXAMPLE 1 PREPARATION OF ACIDIC MORDENITE CATALYST

A crystalline sodium mordenite is selected with the following properties: a $SiO_2/Al_2O_3$ ratio of 15, a $SiO_2/Na_2O$ ratio of 15, a crystallite size of 1000 Å with aggregates ranging in size from 1 micron to 20 microns, a Symmetry Index of 0.97 as determined by X-ray diffraction on a Philips Electronic spectrometer using the $K\alpha 1$ line of copper; and a Langmuir surface area of 303 $m^2/g$. The total pore volume of the sodium mordenite, determined on a Quantachrome Digisorb-6 unit using nitrogen as the adsorbate at 77K, is found to be 0.194 cc/g. The micropore volume, as determined by a t-plot, is found to be 0.046 cc/g. The transitional pore volume, given by the difference (0.194 cc/g–0.046 cc/g), equals 0.148 cc/g, of which 0.083 cc/g are due to mesopores, and 0.065 cc/g are due to macropores.

The sodium mordenite (200 g), described hereinabove, is converted to acidic mordenite via exchange with 2000 ml of 1N aqueous hydrochloric acid at room temperature for thirty minutes. The mordenite-acid slurry is maintained homogeneous by agitation during this period, after which the acid-treated mordenite is isolated by filtration. The filtered solid is washed by suspension in 2000 ml of water, refiltered, and dried in air at 110° C. The dried solid is heated to 700° C. in flowing air for 2 hours. The heated solid is cooled to room temperature in air. The heat-treated acidic mordenite is mixed with 2000 ml of 6N nitric acid and maintained for 2 hours at refluxing temperature under vigorous stirring. After cooling to room temperature the solid is isolated by filtration and washed with water until free of residual acid. The washed solid is dried in air at 110° C. to yield the acidic mordenite catalyst of the invention. Analysis of said catalyst by previously described methods gives the following results: a $SiO_2/Al_2O_3$ ratio of 256/1; a $SiO_2/Na_2O$ ratio of 3732/1; a Symmetry Index of 1.17; a Langmuir surface area of 673 $m^2/g$, a total pore volume of 0.408 cc/g: a micropore volume of 0.208 cc/g: a mesopore volume of 0.068 cc/g: a macropore volume of 0.132 cc/g: and a ratio of combined meso- and macropore volume to total pore volume of 0.49. The catalyst is activated by heating in air at 700° C. for 2 hours.

EXAMPLE 2

Alkylation of Biphenyl

A one-liter stirred tank reactor is equipped with a means for observing and controlling temperature, a means for observing and controlling pressure, and a means for agitating the contents of the reactor. Biphenyl (500 g) and the acidic mordenite catalyst of Example 1 (10 g) are added to the reactor. The reactor is sealed and purged with gaseous propylene. The reactor is pressurized with gaseous propylene to the desired pressure, and then heated with agitation to the desired reaction temperature, as indicated in Table II. As propylene is consumed by the reaction, additional propylene is continuously fed to the reactor so as to maintain the total pressure as indicated. The products are analyzed by gas-phase chromatography. The process conditions and results are set forth in Table II.

TABLE II

| Example | Time (hr) | Temp (°C.) | Pres (psig) | Agitation (rpm) | % Conversion | % p, p'/ ΣDi | % (p, p' + p, m')/ΣDi | % ΣDi/TA | p, p'/ p, m' | % p, p' Yield | % p, p' + p, m' Yield |
|---|---|---|---|---|---|---|---|---|---|---|---|
| 2 (a) | 4 | 250 | 120 | 2000 | 84 | 86 | 96 | 62 | 6.0 | 45 | 54 |
| 2 (b) | 9 | 250 | 120 | 2000 | 98 | 86 | 96 | 71 | 6.0 | 60 | 72 |
| 2 (c) | 20 | 300 | 120 | 2000 | 89 | 48 | 93 | 47 | 1.0 | 20 | 40 |
| 2 (d) | 20 | 250 | 120 | 400–500 | 94 | 52 | 95 | 58 | 1.2 | 28 | 52 |
| 2 (e) | 20 | 250 | 40 | 2000 | 90 | 72 | 97 | 52 | 3.0 | 34 | 45 |
| 2 (f) | 20 | 120 | 15 | 2000 | 70 | 15 | 63 | 26 | 0.3 | 3 | 12 |

"Di" represents dialkylated biphenyls. "Di" is the total number of moles of dialkylated isomers.
"TA" represents the moles of total alkylbiphenyls.

EXAMPLE 3

Preparation of Acidic Mordenite Catalyst

A crystalline sodium mordenite is selected having a $SiO_2/Al_2O_3$ mole ratio of 19.0, and a crystalline size of 1000 Å as aggregates of 2 to 20 microns. The Langmuir surface area and porosity of the sodium mordenite are determined on a Quantachrome Digisorb-6 unit and are found to be the following: Langmuir surface area 378 $m^2/g$; a total pore volume of 0.239 cc/g: a micropore volume of 0.100 cc/g; a mesopore volume of 0.054 cc/g; and a macropore volume of 0.085 cc/g. The Symmetry Index is determined by X-ray diffraction to be 1.26.

The sodium mordenite, described hereinabove, is made into a slurry by adding 200 g of said mordenite to 2000 ml of 1N aqueous hydrochloric acid solution. The slurry is maintained homogeneous by agitation with a magnetic stirring bar. After 30 minutes the acid-treated mordenite is filtered. The acid treatment is repeated twice. The filtered solids are washed by suspension in 2000 ml of deionized water for 30 minutes at room temperature. The washed, acid-exchanged mordenite is filtered. The washing procedure is repeated twice. After the last wash the filtered solids are dried at 110° C. in air overnight to yield 180 g of dried, acidic mordenite. The resulting solid is an acidic mordenite catalyst having a $SiO_2/Al_2O_3$ ratio of 19.6, a Symmetry Index of 1.69, a Langmuir surface area of 600 $m^2/g$, a total pore volume of 0.332 cc/g, a micropore volume of 0.189 cc/g, a mesopore volume of 0.042 cc/g, a macropore volume of 0.101 cc/g, and a combined meso- and macropore volume of 0.430. The catalyst is activated by heating in air at 700° C. for 2 hours.

EXAMPLES 4-8

Alkylation of Biphenyl

A series of reactions is conducted with the catalyst of Example 3 according to the procedure of Example 2, except for varying the alkylating agent. Example 4: propylene is fed into the reactor as a gas at a pressure of 120 psig. Example 5: 1-butene is fed into the reactor as a gas at a pressure of 100 psig. Example 6: 2-butene is fed into the reactor under a vapor pressure of 60 psig. Examples 7 and 8: 1-pentene and 1-hexene, respectively, are fed into the reactor as a liquid with an olefin to biphenyl ratio of about 4. The reaction temperature in all runs is 250° C., the agitation is about 2000 rpm, and the reaction time in all runs is 20 hours. The results are set forth in Table III.

product mixture gives a conversion of 36 percent, a yield of p,p'-dialkylate of 6.1 percent, and a combined yield of p,p'- and p,m'-dialkylates of 7.1 percent. The p,p'/ΣDi factor is 69 percent, the [p,p'+p,m']/ΣDi factor is 80.5 percent, and the ΣDi/TA factor is 24.6 percent.

EXAMPLE 10

Alkylation of Diphenyl Ether

Diphenyl ether (500 g) and the catalyst of Example 1 (10 g) are contacted with propylene at a pressure of 100 psig and a temperature of 250° C. for 20 hours. Analysis of the product mixture gives a conversion of 98.7 percent, a yield of p,p'-dialkylate of 63.4 percent, and a combined yield of p,p'- and p,m'-dialkylates of 75.6 percent. The p,p'/ΣDi factor is 82 percent, the [p,p'+p,m']/ΣDi factor is 95.7 percent, and the ΣDi/TA factor is 80 percent.

EXAMPLE 11

Alkylation of Naphthanlene

Anphthalene (500 g) and the catalyst of Example 1 (10 g) are added to the reactor of Example 2. Propylene gas is added to the reactor to a total pressure of 120 psig. The reactor is heated at 250° C. for 20 hours, while maintaining the pressure at 120 psig. Analysis of the products by gas chromatography gives a conversion of 97.3 percent, a yield of 2,6-dialkylate of 42.7 percent, a yield of 2,7-dialkyalte of 20 percent, and a combined yield of 2,6- and 2,7-dialkylates of 42.7 percent. The 2,6/ΣDi factor is 64 percent, the ]2,6+2,7]/ΣDi factor is 96 percent, and the ΣDi/TA factor is 68 percent, wherein "ΣDi" represents the total moles of dialkylated naphthalenes and "TA" represents the total moles of alkylated products.

EXAMPLE 12

Alkylation of Diphenylmethane

Diphenylmethane (500 g) and the catalyst of Example 1 (10 g) are contacted with propylene at a temperature of 250° C. and a pressure of 120 psig for 20 hours. Analysis of the product mixture gives a conversion of 98.5 percent, a yield of m,m'-dialkylate of 43.8 percent, a yield of p,p'-dialkylate of 25.5 percent, and a combined yield of p,p'- and p,m'-dialkylates of 69.3 percent. The p,p'/ΣDi factor is 34 percent, the [p,p'+p,m']/ΣDi factor is 90 percent, and the ΣDi/TA factor is 77 percent.

EXAMPLE 13

TABLE III

| Example | Olefin | % Conversion | % p, p'/ΣDi | % (p, p' + p, m')/ΣDi | % ΣDi/TA | p, p'/p, m' | % p, p' Yield | % p, p' + p, m' Yield |
|---|---|---|---|---|---|---|---|---|
| 4 | propylene | 90 | 86 | 96 | 62 | 5 | 54 | 64 |
| 5 | 1-butene | 98 | 94 | 98 | 70 | 17 | 68 | 72 |
| 6 | 2-butenes | 92 | 83 | 96 | 66 | 5 | 50 | 61 |
| 7 | 1-pentene | 96 | 63 | 76 | 63 | 5 | 38 | 46 |
| 8 | 1-hexene | 92 | 50 | 60 | 35 | 5 | 27 | 32 |

"Di" represents dialkylated biphenyls. "Di" is the total number of moles of dialkylated isomers.
"TA" represents the moles of total alkylbiphenyls.

EXAMPLE 9

Alkylation of Biphenyl

Biphenyl (50 g) and isopropanol (50 cc) are dissolved in 200 cc of 1,3,5-triisopropylbenzene, and the solution is contacted with the catalyst of Example 3 (10 g) at a temperature of 250° C. for 24 hours. Analysis of the

Preparation of Catalyst

A crystalline acidic mordenite is selected with the following properties: a $SiO_2/Al_2O_3$ ratio of 200, a crystallite size of about 1000 Å with aggregates ranging in size from about 1 micron to about 20 microns, a Symmetry Index of 1.82 as determined by X-ray diffraction on a Philips Electronic spectrometer using the Dα1 line of copper; and a Langmuir surface area of 680 m$^2$/g. The porosity, determined on a Quantachrome Digilab-6 unit, is found to be the following: total pore volume of 0.320 cc/g; micropore volume of 0.203 cc/g; mesopore volume of 0.049 cc/g; macropore volume of 0.068 cc/g; and a ratio of combined meso- and macropore volume to total pore volume of 0.366.

The acidic mordenite solid (100 g), described hereinabove, is heated at 700° C. in flowing air for 2 hours, then cooled to room temperature in air. The cooled acidic mordenite is mixed with 2000 ml of 6N nitric acid and maintained for 2 hours at refluxing temperature under vigorous stirring. After cooling to room temperature the solid is isolated by filtration and washed with water until free of residual acid. The washed solid is dried in air at 110° C. The treatment with heat at 700°) C. and the treatment with 6N nitric acid are repeated one more time. The resulting solid is washed with water until free of residual acid and dried in air at 100° C. to yield the acidic mordenite catalyst of the invention. Analysis of the catalyst by previously described methods gives the following results: a Symmetry INdex of 2.07; a Langmuir surface area of 389 m$^2$/g; a total pore volume of 0.376 cc/g; a micropore volume of 0.149 cc/g; a mesopore volume of 0.075 cc/g; a macropore volume of 0.152 cc/g; and a combined ratio of mesopore and macropore volume to total pore volume of 0.604. The catalyst is activated by heating in air at 700° C. for 2 hours.

EXAMPLE 14

Alkylation of Biphenyl

Biphenyl (500 g) and the catalyst of Example 13 (10 g) are contacted with propylene at a pressure of 120 psig and a temperature of 250° C. for 20 hours. Analysis of the product mixture gives a biphenyl conversion of 98 percent, a yield of p,p'-dialkylate of 68 percent, and a combined yield of p,p'- and p,m'-dialkylates of 75.3 percent. The p,p'/ΣDi factor is 86 percent, the [p,p'+p,m']/ΣDi factor is 96 percent, and the ΣDi/Ta factor is 80 percent.

EXAMPLE 15

Preparation of Catalyst

A crystalline sodium mordenite is selected having a SiO$_2$/Al$_2$O$_3$ mole ratio of 19, and a crystalline size of 2000 Å as aggregates of 2 and 20 microns. The Langmuir surface area and porosity of the sodium mordenite are determined on a Quantachrome Digisorb-6 unit and are found to be the following: Langmuir surface area 378 M$^2$/g; a total pre volume of 0.239 cc/g; a micropore volume of 0.100 cc/g; a mesopore volume of 0.054 cc/g; and a macropore volume of 0.085 cc/g. The Symmetry Index is determined by X-ray diffraction to be 1.26.

The sodium mordenite, described hereinabove, is made into a slurry by adding 20 g of said mordenite to 2000 ml of 1N aqueous ammonium nitrate solution. The slurry is maintained homogeneous by agitation with a magnetic stirring bar. After 30 minutes the ammonium-treated mordenite is filtered. The ammonium treatment is repeated twice. The filtered solids are washed by suspension in 2000 ml of deionized water for 30 minutes at room temperature. The washed, ammonium-exchanged mordenite is filtered. The washing procedure is repeated twice. After the last wash the filtered solids are dried at 110° C. in air overnight to yield 19 g of dried, acidic mordenite. The resulting solid is an acidic mordenite catalyst having a SiO$_2$/Al$_2$O$_3$ ratio of 19, A symmetry Index of 1.36, a Langmuir surface area of 270 m$^2$/g, a total pore volume of 0.228 cc/g, a micropore volume of 0.109 cc/g, a mesopore volume of 0.038 cc/g, a macropore volume of 0.109 cc/g, and a combined meso- and macropore volume of 0.119. The catalyst is activated by heating in air at 400° C. for 2 hours.

EXAMPLE 16

Alkylation of Biphenyl

Biphenyl (500 g) and the catalyst of Example 15 (10 g) are contacted with propylene at a pressure of 120 psig and a temperature of 270° C. for 20 hours. Analysis of the product mixture gives a biphenyl conversion of 99 percent and a combined yield of p,p'-and p,m'-diialkylates of 63.1 percent. The [p,p'+p,m']/ΣDi factor is 94 percent, and ΣDi/TA factor is 68 percent. The p,p'/p,m' ratio is 1.6

What is claimed is:

1. A process of alkylating a polycyclic aromatic compound to a mixture of substituted polycyclic aromatic compounds enriched in the linear- and near linear-alkylated isomers comprising contacting a polycyclic aromatic compound with an alkylating agent in the presence of a catalyst comprising an acidic mordenite zeolite having a silica/alumina molar ratio of between about 15:1 and about 300:1 and having a crystalline structure which is determined by X-ray diffraction to have a Symmetry Index in the range from about 1.0 to about 2.0, the contacting occurring at a temperature in the range from about 200° C. to about 350° C. and an alkene pressure in the range from about 10 psig to about 150 psig, such that a mixture of substituted polycyclic aromatic compounds enriched in the linear- and near linear-alkylated isomers is formed.

2. The process of claim 1 wherein the polycyclic aromatic compound is a C$_{10}$-C$_{24}$ fused or non-fused aromatic compound.

3. The process of claim 2 wherein the non-fused polycyclic aromatic compound is represented by the formula:

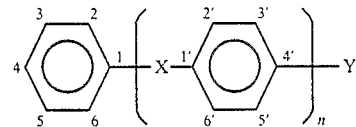

wherein n is a positive number from 1 to 3; Y is hydrogen, hydroxyl, sulfhydryl, alkyl of C$_{1-10}$ carbon atoms, aliphatic alkoxy or thioalkoxy of C$_{1-10}$ carbon atoms, fluoro, chloro, or bromo; and X is absent or is O, S, SO, SO$_2$, CH$_2$, CH$_2$CH$_2$, CH$_2$CH$_2$CH$_2$ or CHCH$_3$.

4. The process of claim 2 wherein the non-fused polycyclic aromatic compound is represented by the formula:

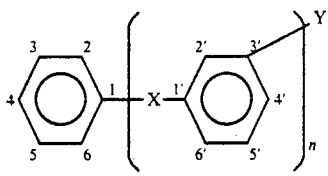

wherein n is a positive number from 1 to 3; Y is hydrogen, hydroxyl, sulfhydryl, alkyl of $C_{1-10}$ carbon atoms, aliphatic alkoxy or thioalkoxy of $C_{1-10}$ carbon atoms, fluoro, chloro, or bromo; and X is absent or is O, S, SO, $SO_2$, $CH_2$, $CH_2CH_2$, $CH_2CH_2CH_2$ or $CHCH_3$.

5. The process of claim 2 wherein the polycyclic aromatic compound is biphenyl, naphthalene, or diphenyl ether.

6. The process of claim 5 wherein the polycyclic aromatic compound is biphenyl.

7. The process of claim 5 wherein the polycyclic aromatic compound is naphthalene.

8. The process of claim 1 wherein the alkylating agent is a monoolefin, a diolefin, or an alcohol.

9. The process of claim 8 wherein the monoolefin is propylene, n-butene, 1-hexane, cyclohexene, or 1-octene.

10. The process of claim 9 wherein the olefin is propylene.

11. The process of claim 9 wherein the olefin is n-butene.

12. The process of claim 1 wherein the temperature is in the range from about 250° C. to about 300° C.

13. The process of claim 1 wherein the alkylating agent is diluted with an inert gas.

14. The process of claim 1 wherein the polycyclic aromatic compound is dissolved in a solvent.

15. The process of claim 1 wherein the extrudate size of the catalyst is in the range from about 1/32 inch to about ½ inch in diameter.

16. The process of claim 1 wherein the alkene pressure is in the range from about 10 psig to about 50 psig.

17. The process of claim 1 wherein the yield of dialkylates is at least about 30 percent.

18. The process of claim 1 wherein the catalyst has an extrudate size in the range from about 1/32 inch to about ½ inch in diameter, a silica/alumina molar ratio of between about 15:1 and about 50:1, a Symmetry Index of between about 1.5 and 2.0, and a porosity such that the total pore volume is in the range from about 0.18 cc/g to about 0.45 cc/g and the ratio of the combined meso- and macropore volume to the total pre volume is in the range from about 0.25 to about 0.75.

19. The process of claim 1 wherein the selectivity to linear-alkylated isomers is at least about 50 mole percent.

20. The process of claim 1 wherein the selectivity to linear-alkylated isomers is at least about 50 mole percent.

21. The process of claim 1 wherein the combined moles of p,p' and p,m' isomers relative to the total number of moles of dialkylates, as represented by the fraction $(p,p'+p,m')/\Sigma Di$, is at least about 60 mole percent.

22. The process of claim 1 wherein the combined moles of p,p' and p,m' isomers relative to the total number of moles of dialkylates, as represented by the fraction $(p,p'+p,m')/\Sigma Di$, is at least about 70 mole percent.

23. The process of claim 1 wherein the combined moles of p,p' and p,m' isomers relative to the total number of moles of dialkylates, as represented by the fraction $(p,p'+p,m')/\Sigma Di$, is at least about 90 mole percent.

24. The process of claim 1 wherein the combined selectivity to linear- and near linear-alkylated isomers is at least about 45 mole percent.

25. The process of claim 1 wherein the combined selectivity to linear- and near linear-alkylated isomers is at least about 60 mole percent.

26. The process of claim 1 wherein the combined selectivity to linear- and near linear-alkylated isomers is at least about 20 mole percent.

27. The process of claim 26 wherein the combined yield of linear- and near linear-alkylated isomers is at least about 55 mole percent.

28. The process of claim 27 wherein the combined yield of linear- and near linear-alkylated isomers is at least about 70 mole percent.

29. A process of alkylating biphenyl to a mixture of disubstituted products enriched in 4,4'- and 4,3'-(dialkylate)-1,1'-biphenyl comprising contacting biphenyl with an alkylating agent in the presence of a catalyst at a temperature in the range from about 200° C. to about 350° C. and a pressure in the range from about 10 psig to about 150 psig such that the 4,4'- and 4,3'-dialkylated isomer is formed in a combined yield of at least about 40 percent, said catalyst comprising an acidic mordenite zeolite having a silica/alumina molar ratio of between about 15:1 and 300:1 and a crystalline structure which is determined by X-ray diffraction to have a Symmetry Index in the range from about 1.0 to about 2.0.

* * * * *

UNITED STATES PATENT AND TRADEMARK OFFICE
CERTIFICATE OF CORRECTION

PATENT NO. : 5,015,797

DATED : May 14, 1991

INVENTOR(S) : Guo-shuh J. Lee, Juan M. Garces, and Joseph J. Maj

It is certified that error appears in the above-identified patent and that said Letters Patent is hereby corrected as shown below:

Column 26, Claim 18, line 1, " total pre volume " should correctly read -- total pore volume --.

Column 26, Claim 19, line 4, " about 50 mole " should correctly read -- about 20 mole --.

Column 26, Claim 26, line 29, delete " selectivity to " and insert -- yield of the --.

Signed and Sealed this

Twenty-ninth Day of December, 1992

Attest:

DOUGLAS B. COMER

*Attesting Officer*    Acting Commissioner of Patents and Trademarks